United States Patent [19]

Domagala et al.

[11] Patent Number: 4,840,956

[45] Date of Patent: Jun. 20, 1989

[54] NOVEL DISUBSTITUTED-7-PYRROLIDINOQUINOLINE ANTIBACTERIAL AGENTS

[75] Inventors: John M. Domagala, Canton; Susan E. Hagen, Ypsilanti; Joseph P. Sanchez, Canton, all of Mich.; Marjorie S. Solomon, Bellevue, Wash.

[73] Assignee: Warner-Lambert Company, Morris Plains, N.J.

[21] Appl. No.: 144,301

[22] Filed: Jan. 14, 1988

Related U.S. Application Data

[63] Continuation-in-part of Ser. No. 831,232, Feb. 18, 1986, abandoned.

[51] Int. Cl.[4] .................. A61K 31/47; C07D 401/04
[52] U.S. Cl. ........................... 514/312; 546/156; 548/531; 548/537; 548/557; 548/566
[58] Field of Search .............. 546/156; 514/312

[56] References Cited

U.S. PATENT DOCUMENTS

| | | | |
|---|---|---|---|
| 4,556,658 | 12/1985 | Grohe et al. | 544/358 |
| 4,578,473 | 3/1986 | Domagala et al. | 546/156 |
| 4,620,007 | 10/1986 | Grohe et al. | 546/156 |
| 4,665,079 | 5/1987 | Culbertson et al. | 514/312 |
| 4,735,949 | 4/1988 | Domagala et al. | 514/300 |

FOREIGN PATENT DOCUMENTS

| | | |
|---|---|---|
| 0132845 | 2/1985 | European Pat. Off. |
| 59-010580 | 1/1984 | Japan. |
| 59-29685 | 2/1984 | Japan. |

OTHER PUBLICATIONS

Abstract for JP 60/126284 (7/5/85).
Abstract for JP 59/010580 (1/20/84).
Tsukamoto et al., Chemical Abstracts, vol. 106, No. 67135y (1987).
Koga et al., *J. Med. Chem.* 23, pp. 1358–1363 (1980).
Domagala et al., *J. Med. Chem.* 29 pp. 445–448 (1986).

*Primary Examiner*—Donald G. Daus
*Assistant Examiner*—E. Bernhardt
*Attorney, Agent, or Firm*—Francis J. Tinney

[57] ABSTRACT

Disubstituted 7-pyrrolidinoquinoline- and -napthylridine-3-carboxylic acids as antibacterial agents are described as well as methods for their manufacture, formulation, and use in treating bacterial infections.

5 Claims, No Drawings

NOVEL DISUBSTITUTED-7-PYRROLIDINOQUINOLINE ANTIBACTERIAL AGENTS

This is a continuation-in-part of United States Application Ser. No. 831,232, filed Feb. 18, 1986, now abandoned.

BACKGROUND OF THE INVENTION

European Patent Publication No. 106,489 describes 7-alkylaminoalkyl-, 7-aminoalkyl- and 7-aminopyrrolidinoquinoline, and -naphthyridine-3-carboxylic acids as antibacterial agents.

U.S. Pat. No. 4,556,658 describes in general 7-amino-1-cyclopropyl-6,8-difluoro-1,4-dihydro-4-oxoquinoline-3-carboxylic acids where amino can be, among many other substituents, a five-membered or six-membered heterocyclic ring optionally monosubstituted, disubstituted, or trisubstituted at the carbon atoms by $C_1$–$C_4$ alkyl, hydroxyl, alkoxy having one to three carbon atoms, amino, methylamino, or ethylamino, and each carbon atom can carry only one substituent also as antibacterial agents.

The present invention provides new quinolones and naphthyridines where the 7-amino group is a disubstituted pyrrolidine having an aromatic radical as one substituent and an amino or aminomethyl radical as the second substituent on the same or different carbon atom. These new compounds are useful as broad spectrum antibacterial agents and are especially active against gram-positive bacteria.

SUMMARY OF THE INVENTION

Accordingly, the present invention relates to novel disubstituted-7-pyrrolidinoquinoline- and -naphthyridine-3-carboxylic acids of the Formula I

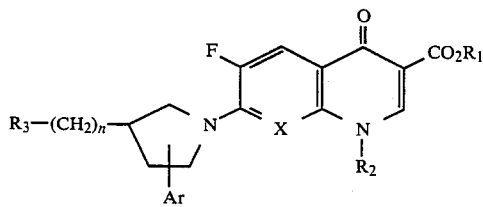

wherein X is CH, CF, or N; $R_1$ is hydrogen or alkyl having one to six carbon atoms; $R_2$ is alkyl having one to four carbon atoms, vinyl, haloalkyl or hydroxyalkyl having two to four carbon atoms, or cycloalkyl having three to six carbon atoms; n is zero to three; $R_3$ is $OR_4$ or $NR_4R_5$, in which $R_4$ and $R_5$ are each independently hydrogen or alkyl having one to six carbon atoms; Ar is phenyl or phenyl substituted by alkyl having one to four carbon atoms, halogen, trifluoromethyl, $OR_4$ or $NR_4R_5$, and the pharmaceutically acceptable acid addition or base salts thereof.

The invention includes an antibacterial composition comprising an antibacterially effective amount of a compound of the Formula I defined above together with a pharmaceutically acceptable carrier or diluent.

The invention also includes a method for treating bacterial infections in a mammal suffering therefrom which comprises administering to a mammal the above defined pharmaceutical composition in unit dosage form.

DETAILED DESCRIPTION OF THE PREFERRED EMBODIMENTS

The compounds of the present invention and of Formula I may be prepared by reacting a compound of the Formula II

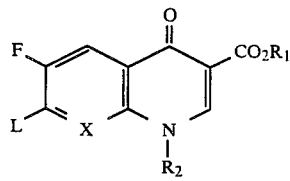

with an appropriate pyrrolidine of the Formula III

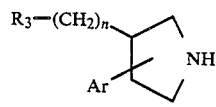

wherein all of the terms are as defined above for Formula I and L is fluorine or chlorine. For purposes of this reaction, the $R_3$ substituent, when $R_4$ is hydrogen, may, if desired, be protected by a group which renders it substantially inert to the reaction conditions.

Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound II and Compound III, if desired, by procedures known to those skilled in the art. For example, the ethoxycarbonyl group may be removed by acid or base hydrolysis and the trityl group may be removed by hydrogenolysis.

The reaction between the compound of structural Formula II and a suitably protected compound of Formula III may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of Formula III may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° C. to about 150° C.; higher temperatures usually require shorter reaction times.

The removal of the protecting group may be accomplished either before or after isolating the product, I. Alternatively, the protecting group need not be removed.

The starting compounds having structural Formulae II and III are known in the art or, if new, may be prepared from known starting materials by standard procedures or by variations thereof. Thus, the following compounds are disclosed in the noted references:

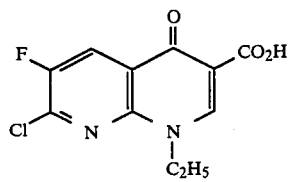

European Patent Application 80 40 1369

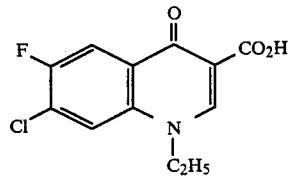

J. Med. Chem., 23, 1358

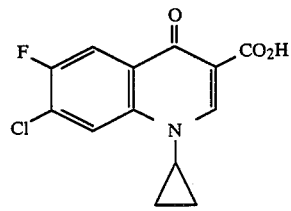

European Patent Application 0078362

European Patent 0 000 203

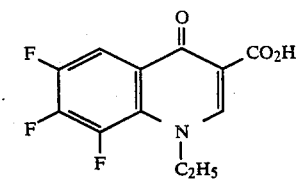

British Patent 2,057,440

1Cyclopropyl-6,7,8-trifluoro-1,4-dihydro-4-oxo-3-quinolinecarboxylic acid may be prepared by a series of reactions starting from 2,3,4,5-tetrafluorobenzoic acid. The sodium salt of 2,3,4,5-tetrafluorobenzoic acid is reacted with oxalyl chlorine and the product condensed with diethyl malonate in the presence of magnesium turnings to afford after hydrolysis 2,3,4,5-tetrafluorobenzoylacetic acid, ethyl ester. This compound is, in turn, treated with triethylorthoformate and acetic anhydride, followed by cyclopropylamine to afford 2-(2,3,4,5-tetrafluorobenzoyl)-2-cyclopropylaminoacrylic acid, ethyl ester, which is then ring closed and hydrolysed with sodium hydride to give the desired intermediate.

7Chloro-1-cyclopropyl-6-fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3-carboxylic acid can be converted to the 7-hydroxy derivative with a mixture of nitric and sulfuric acids which is then replaced by chlorine by treatment with phosphorous oxychloride to give the desired intermediate.

The starting pyrrolidines of Formula III may be prepared as illustrated in the Examples.

Preferred compounds of the present invention are those of Formula I, wherein X is CH, CF, or N; $R_1$ is hydrogen or alkyl having one to six carbon atoms; $R_2$ is ethyl, vinyl, 2-fluoroethyl, hydroxyethyl or cyclopropyl; n is zero or one; $R_3$ is OH, $NH_2$, methylamino, dimethylamino, ethylamino or diethylamino; Ar is phenyl or phenyl substituted by methyl, methoxy, fluorine, chlorine, hydroxy, trifluoromethyl, amino, methylamino, dimethylamino, ethylamino or diethylamino, and the pharmaceutically acceptable acid addition or base salts thereof.

More preferred are compounds of Formula I, wherein X is CF or N; $R_1$ is hydrogen, methyl or ethyl; $R_2$ is ethyl, vinyl, 2-fluoroethyl or cyclopropyl; $R_3$ is OH or $NH_2$; Ar is phenyl or phenyl substituted by methyl, methoxy, fluorine, chlorine, hydroxy, trifluoromethyl or amino, and the pharmaceutically acceptable acid addition or base salts thereof.

Most preferred are compounds of Formula I, wherein X is CF or N; $R_1$ is hydrogen; $R_2$ is cyclopropyl; $R_3$ is OH or $NH_2$; Ar is phenyl, and the pharmaceutically acceptable acid addition or base salts thereof.

Preferred quinoline compounds of the present invention are those of Formula I wherein $R_1$ is hydrogen or alkyl of one to six carbon atoms; $R_2$ is alkyl of one to four carbon atoms, vinyl, haloalkyl or hydroxyalkyl of two to four carbon atoms, or cycloalkyl of three to six carbon atoms; n is zero to three; $R_3$ is $OR_4$ or $NR_4R_5$, in which $R_4$ and $R_5$ are each independently hydrogen or alkyl of one to six carbon atoms; Ar is phenyl or phenyl substituted by alkyl of one to four carbon atoms, halogen, trifluoromethyl, $OR_4$ or $NR_4R_5$, and the pharmaceutically acceptable acid addition or base salt thereof.

More preferred quinoline compounds of the present invention are compounds of Formula I wherein $R_2$ is cyclopropyl; n is zero or one; $R_3$ is OH, $NH_2$, methylamino, dimethylamino, ethylamino, or diethylamino, and Ar is phenyl or phenyl substituted by halogen, $OR_4$ or $NR_4R_5$, and the pharmaceutically acceptable acid addition or base salts thereof.

Most preferred quinoline compounds of the present invention are compounds of Formula I wherein $R_1$ is hydrogen; $R_2$ is cyclopropyl, and Ar is phenyl, and the pharmaceutically acceptable acid addition or base salts thereof.

Particularly valuable are the following:

7-[(3-amino-3-phenyl)-1-pyrrolidinyl]-1-cyclopropyl-6,8-difluoro-1,4-dihydro-4-oxo-3-quinolinecarboxylic acid;

7-[[3-(aminomethyl)-4-phenyl]-1-pyrrolidinyl]-1-cyclopropyl-6,8-difluoro-1,4-dihydro-4-oxo-3-quinolinecarboxylic acid;

7-[(3-amino-4-phenyl)-1-pyrrolidinyl]-1-cyclopropyl-6,8-difluoro-1,4-dihydro-4-oxo-3-quinolinecarboxylic acid;

1-cyclopropyl-6,8-difluoro-1,4-dihydro-7-[(3-hydroxy-3-phenyl)-1-pyrrolidinyl]-4-oxo-3-quinolinecarboxylic acid; and 7-[[3-(aminomethyl)-3-phenyl]-1-pyrrolidinyl]-1-cyclopropyl-6,8-difluoro-1,4-dihydro-4-oxo-3-quinolinecarboxylic acid.

The compounds of the invention display antibacterial activity when tested by the microtitration dilution method as described in Heifetz, et al, *Antimicr. Agents & Chemoth.*, 6, 124 (1974), which is incorporated herein by reference.

By use of the above referenced method, the following minimum inhibitory concentration values (MICs in $\mu g/ml$) were obtained for representative compounds of the invention. Especially potent antibacterial activity is demonstrated against the gram-positive bacteria tested, e.g., the Staphylococcus and Streptococcus bacteria.

| | IN VITRO ANTIBACTERIAL ACTIVITY Minimal Inhibitory Concentration MIC ($\mu g/ml$) | | | | |
|---|---|---|---|---|---|
| Organisms | Compound Example 1 | Compound Example 2 | Compound Example 3 | Compound Example 4 | Compound Example 5 |
| *Enterobacter cloacae* MA 2646 | 0.05 | 0.2 | 0.2 | 0.1 | 0.05 |
| *Escherichia coli* Vogel | 0.05 | 0.1 | 0.1 | 0.1 | 0.05 |
| *Klebsiella pneumoniae* MGH-2 | 0.1 | 0.1 | 0.2 | 0.1 | 0.1 |
| *Proteus rettgeri* M 1771 | 0.1 | 0.4 | 0.4 | 0.1 | 0.2 |
| *Pseudomonas aeruginosa* UI-18 | 0.4 | 1.6 | 1.6 | 0.1 | 0.4 |
| *Staphylococcus aureus* H 228 | 0.006 | 0.013 | 0.05 | 0.003 | 0.025 |
| *Staphylococcus aureus* UC-76 | 0.006 | 0.006 | 0.025 | 0.003 | 0.013 |
| *Streptococcus faecalis* MGH-2 | 0.05 | 0.013 | 0.1 | 0.025 | 0.05 |
| *Streptococcus pneumoniae* SV-1 | 0.025 | 0.006 | 0.1 | 0.013 | 0.013 |
| *Streptococcus pyogenes* C-203 | 0.05 | 0.013 | 0.1 | 0.05 | 0.05 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylflucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicyclic, malic, gluconic, fumaric, succinic, ascorbic, maleic, methanesulfonic, lactic, and the like. The salts are prepared by contacting the free base form with a sufficient amount of the desired acid to produce either a mono or di, etc., salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about six carbon atoms except when otherwise specifically stated. Representative of such groups are methyl, ethyl, propyl, isopropyl, butyl, sec.-butyl, isobutyl, tert.-butyl, amyl, isoamyl, neopentyl, hexyl, and the like.

The cycloalkyl groups contemplated by the invention comprise those having three to six carbon atoms such as cyclopropyl, cyclobutyl, cyclopentyl, and cyclohexyl.

The alkoxy groups contemplated by the invention comprise both straight and branched carbon chains of from one to about four carbon atoms unless otherwise specified. Representative of such groups are methoxy, ethoxy, propoxy, i-propoxy, t-butoxy, and the like.

The term, haloalkyl, is intended to include halogen substituted straight and branched carbon chains of from two to four carbon atoms. Those skilled in the art will recognize that the halogen substituent may not be present on the $\alpha$-carbon atom of the chain. Representative of such groups are $\beta$-fluoroethyl, $\beta$-chloroethyl, $\beta,\beta$-dichloroethyl, $\beta$-chloropropyl, $\beta$-chloro-2-propyl, $\lambda$-iodobutyl, and the like.

The term halogen is intended to include fluorine, chlorine, bromine, and iodine unless otherwise specified.

Certain substituents on the pyrrolidine ring may exist in the cis or trans stereochemical forms. The pure isomers or mixtures thereof are contemplated by the invention.

Certain compounds of the invention may exist in optically active forms. The pure R isomers, pure S isomers as well as mixtures thereof; including the racemic mixtures, are contemplated by the invention. Additional assymmetric carbon atoms may be present in a substituent such as an alkyl group. All such isomers as well as mixtures thereof are intended to be included in the invention.

The compounds of the invention can be prepared and administered in a wide variety of oral, parenteral, and topical dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersable granules, capsules, cachets, suppositories, and ointments. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions, and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of Formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel, or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor' preferred methods for preparing the compounds of the invention.

EXAMPLE 1

7-[(3-Amino-3-phenyl)-1-pyrrolidinyl]-1-cyclopropyl-6,8-difluoro-1,4-dihydro-4-oxo-3-quinolinecarboxylic acid To the 0.78 g (4.8 mmol) of 3-phenyl-3-aminopyrrolidine was added 0.7 g (4.8 mmol) of 1,8 diazabicyclo-[5.4.0]undec-7-ene and 15 ml of acetonitrile. Then 1.3 g (4.5 mmol) of 1-cyclopropyl-6,7,8-trifluoro-1,4-dihydro-4-oxo-3-quinolinecarboxylic acid was added and the reaction mixture heated to reflux for one hour. The precipitate that formed was filtered and washed with ether. The solids were then dissolved in 5 ml of water and the pH taken to 2.5 with 2N hydrochloric acid. The resulting precipitate was filtered and washed with ether to afford 1.2 g of 7-[(3-amino-3-phenyl)-1-pyrrolidinyl]-1-cyclopropyl-6,8-difluoro-1,4-dihydro-4-oxo-3-quinolinecarboxylic acid.

EXAMPLE 2

7-[[3-(Aminomethyl)-4-phenyl]-1-pyrrolidinyl]-1-cyclopropyl-6,8-difluro-1,4-dihydro-4-oxo-3-quinolinecarboxylic acid A suspension of 1.0 g (3.53 mmole) of 1-cyclo-propyl-6,7,8-trifluoro-1,4-dihydro-4-oxo-3-quinoline carboxylic acid, 30 ml of acetonitrile, 0.35 g (3.5 mmole) of triethylamine, and 0.65 g (3.7 mmole) of 4-phenyl-3-pyrrolidinemethanamine is refluxed for four hours, then stirred at room temperature overnight. The reaction mixture is filtered and the precipitate washed with ethyl ether until dry to give the title compound.

EXAMPLE 3

7-[(3-Amino-4-phenyl)-1-pyrrolidinyl]-1-cyclopropyl-6,8-difluoro-1,4-dihydro-4-oxo-3-quinolinecarboxylic acid A suspension of 1.13 g (4.0 mmole) of 6,7,8-trifluoro-1,4-dihydro-4-oxo-3-quinolinecarboxylic acid, 0.97 g (6.0 mmole) of a mixture of cis- and trans-4-phenyl-3-pyrrolidinamine [*Monatshefte Chimie*, 94, 1241 (1963)], 1.0 g (10 mmole) of triethylamine and 100 ml of acetonitrile was heated at reflux for four hours. The reaction was cooled to 5° C., the precipitate removed by filtration, washed with acetonitrile, then ether, and dried in vacuo to give 1.3 g of the title compound, mp 185°–187° C.

EXAMPLE 4

1-Cyclopropyl-6,8-difluoro-1,4-dihydro-7-[(3-hydroxyl-3-phenyl)-1-pyrrolidinyl]-4-oxo-3-quinolinecarboxylic acid To 0.8 g (2.8 mmol) of the 1-cyclopropyl-6,7,8-trifluro-1,4-dihydro-4-oxo-3-quinolinecarboxylic acid was added 15 ml of dry N,N-dimethylformamide, 0.56 ml (one equivalent) of the 3-hydroxy-3-phenylpyrrolidine, and 0.78 ml (one equivalent) of triethylamine. The mixture was heated to 50° C. for 18 hours. Concentration and addition of water at pH 4 gave a precipitate which was filtered to yield 1.11 g of the title compound, mp 242°–245° C.

EXAMPLE 5

7-[[3-(Aminomethyl)-3-phenyl]-1-pyrrolidinyl]-1-cyclopropyl-6,8-difluro-1,4-dihydro-4-oxo-3-quinolinecarboxylic acid A suspension of 1.13 g (4.00 mmol) of 1-cyclopropyl-6,7,8-trifluoro-1,4-dihydro-4-oxo-3-quinolinecarboxylic acid, 40 ml of acetonitrile, 1.03 g (10.0 mmol) of triethylamine, and 0.88 g (5.00 mmol) of 3-phenyl-3-pyrrolidinemethanamine was refluxed for 4 hours, then cooled to room temperature. The solids were filtered and washed with acetonitrile and ether to give 1.55 g of the title compound, mp 233°–235° C.

PREPARATION OF STARTING MATERIALS

EXAMPLE A

4-Phenyl-3-pyrrolidinemethanamine

4-Phenyl-1-(phenylmethyl)-3-pyrrolidinemethanamine

To a solution of 5.7 g (0.022 mole) of trans-4-phenyl-1-(phenylmethyl)-3-pyrrolidinecarbonitrile (*Helv. Chim. Acta*, 64, 2203 (1981)) in 30 ml tetrahydrofuran was added 0.83 g (0.022 mmol) of lithium aluminum hydride in portions under nitrogen. The reaction mixture was then stirred at room temperature for 18 hours. To the resulting suspension were added 1 ml of water, 0.8 ml of 40% sodium hydroxide, and 3 ml of water. The grainy precipitate was filtered and washed with tetrahydrofuran. The combined filtrates were concentrated to give 5.5 g of 4-phenyl-1-(phenylmethyl)-3-pyrrolidinemethanamine.

This material was used without further purification in the next step.

4-Phenyl-3-pyrrolidinemethanamine

A mixture of 4.79 g (0.018 mole) of 4-phenyl-1-(phenylmethyl)-3-pyrrolidinemethanamine, 0.7 g of 20% palladium on carbon, and 250 ml of methanol was shaken in an atmosphere of hydrogen at about 50 psi and at room temperature for 24 hours. The catalyst was filtered and the filtrate evaporated under reduced pressure to give 2.74 g of 4-phenyl-3-pyrrolidinemethanamine.

EXAMPLE B

3-Phenyl-3-pyrrolidine amine

3-Phenyl-1-[(phenylmethoxy)carbonyl]-3-hydroxypyrrolidine

A mixture of 8.0 g (0.027 mol) 3-phenyl-3-hydroxypyrrolidine hydrochloride (Ger. 1,144,279 (Cl.12p) Feb. 29, 1963), 1.0 g of 20% palladium on carbon, and 100 ml of ethanol was shaken in an atmosphere of hydrogen at 50 psi for three hours. The catalyst was filtered and the filtrate evaporated under reduced pressure to give 5.15 g of residue which was used without purification in the next step.

To a stirring solution of 5.0 ml (0.042 mol) of benzyl chloroformate in 5.0 ml of dry tetrahydrofuran under nitrogen, was added at −10° C. the 5.15 g of residue from the reaction above and 4.4 ml (0.031 mol) of triethylamine in 50 ml of dry tetrahydrofuran. The reaction mixture was allowed to warm to room temperature and stir for 18 hours. After dilution with 500 ml of ether the organic layer was extracted twice with hydrochloric acid pH 2.5. The ether layer was then dried over magnesium sulfate, filtered, and the solvent removed at reduced pressure. The resulting oil was tritrated with ether-hexane to give 2.72 g of 3-phenyl-1-(phenylmethoxy)carbonyl)-3-hydroxypyrrolidine, mp 117°–120° C.

3-Phenyl-3-pyrrolidine amine

To a mixture of 2.03 g (6.0 mmol) 3-phenyl-1-[(phenylmethoxy)carbonyl]-3-hydroxypyrrolidine, 22.0 ml of trifluoroacetic acid and 3.5 ml of water at 0° C. was added 2.80 g (43 mmol) of sodium azide. The reaction mixture was taken to room temperature, stirred for two hours, then quenched slowly with 100 ml of ammonium hydroxide. After extraction of the ammonium hydroxide twice with chloroform the organic layers were combined, dried over magnesium sulfate, filtered, and the solvent evaporated at reduced pressure. The resulting oil was chromatographed to give 1.7 g of crude product which was used without purification in the next step (IR=2100 cm$^{-1}$).

A mixture of 1.7 g of crude product from the above reaction, 0.5 g of 20% palladium on carbon, and 100 ml of ethanol was shaken at 50 psi for four hours. The catalyst was filtered and the filtrate evaporated under reduced pressure to give 0.78 g of 3-phenyl-3-pyrrolidine amine as an oil, which was used without further purification.

EXAMPLE C

3-Phenyl-3-pyrrolidinemethanamine 3-phenyl-1-(phenylmethyl)-3-pyrrolidinecarboxamide A suspension of 53.4 g (0.23 mol) of N-benzyl-N-(cyanomethyl)-N-[(trimethylsilyl)methyl]amine (*J. Org. Chem.*, 50, 4006 (1985)), 41.2 g (0.25 mol) of methyl atropate, 32.2 g (0.25 mol) of silver fluoride and 1 l of acetonitrile was stirred overnight at room temperature in the dark. The mixture was diluted with chloroform and filtered through celite. Concentration of the filtrate gave an oil which was chromatographed on silica gel, eluting with an 80:20 chloroform:ethyl acetate mixture, to give 27.9 g of methyl 3-phenyl-1-(phenylmethyl)-3-pyrrolidinecarboxylate.

A solution of 11.9 g (0.040 mol) of the ester isolated above and the 150 ml of 6N hydrochloric acid was refluxed for 2.5 hours and stirred at room temperature overnight. The solids were filtered, washed with water and ether, and recrystallized from isopropanol to give 10.0 g of the pyrrolidine acid, mp 228°–230° C., as the hydrochloride salt.

This material was suspended in 400 ml of acetonitrile, treated with 3.18 g (0.031 mol) of triethylamine, and stirred at room temperature for one hour. To this solution was added 5.53 g (0.034 mol) of 1,1'-carbonyldiimidazole portionwise, and the reaction mixture was stirred at 60° C. for 90 minutes, then cooled to room temperature. A steady stream of ammonia was bubbled through the solution for 30 minutes. The mixture was concentrated, and the residue was dissolved in methylene chloride, washed with water, and dried over magnesium sulfate. Concentration gave the title compound as a white solid, mp 88°–90° C.

3-Phenyl-3-pyrrolidinemethanamine

To a solution of 3.1 g (0.011 mol) of 3-phenyl-1-(phenylmethyl)-3-pyrrolidinecarboxamide in 150 ml of dry tetrahydrofuran was added 0.84 g (0.022 mol) of lithium aluminum hydride in portions under argon. The suspension was stirred overnight at room temperature. To the mixture was added 0.7 ml of water, 0.9 ml of 40% sodium hydroxide, and 3.0 ml of water. The grainy precipitate was filtered, and the filtrate was concentrated to give 2.9 g of 3-phenyl-1-(phenylmethyl)-3-pyrrolidinemethanamine. A solution of the residue from the above reaction, 0.5 g of 20% palladium on carbon, and 100 ml of methanol was shaken in an atmosphere of hydrogen at 50 psi for 18 hours. The catalyst was filtered and the filtrate concentrated to give 1.8 g of the title compound.

We claim:

1. A compound having the formula

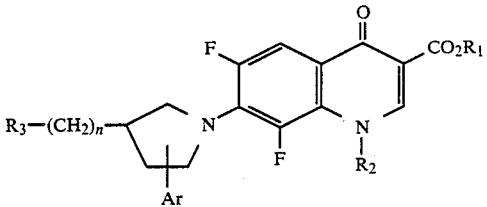

wherein $R_1$ is hydrogen or alkyl of one to six carbon atoms; $R_2$ is cyclopropyl; n is zero $R_3$ is $OR_4$, in which $R_4$ is hydrogen or alkyl of one to six carbon atoms; Ar is phenyl; or a pharmaceutically acceptable acid addition or base salt thereof.

2. A compound according to claim 1, wherein $R_1$ is hydrogen.

3. A compound according to claim 2 and being 1-cyclopropyl-6,8-defluoro-1,4-dihydro-7-[(3-hydroxy-3-phenyl)-1-pyrrolidinyl]-4-oxo-3-quinolinecarboxylic acid.

4. An antibacterial composition comprising an antibacterially effective amount of a compound as claimed in claim 1 together with a pharmaceutically acceptable carrier or diluent.

5. A method of treating bacterical infections in a mammal which comprises administering to said mammal suffering therefrom an antibacterial composition as claimed in claim 4.

* * * * *

UNITED STATES PATENT AND TRADEMARK OFFICE
CERTIFICATE OF CORRECTION

PATENT NO. : 4,840,956
DATED : June 20, 1989
INVENTOR(S) : Domagala et al.

It is certified that error appears in the above—identified patent and that said Letters Patent is hereby corrected as shown below:

In column 12, line 19,
 delete "defluoro" and
 insert -- difluoro --.

In column 12, line 26,
 delete "bacterical" and
 insert -- bacterial --.

Signed and Sealed this

Twentieth Day of March, 1990

*Attest:*

JEFFREY M. SAMUELS

*Attesting Officer*     *Acting Commissioner of Patents and Trademarks*